US012757843B2

(12) United States Patent
Ishikawa

(10) Patent No.: US 12,757,843 B2
(45) Date of Patent: Oct. 13, 2026

(54) SEEDLING, METHOD FOR GROWING SEEDLING, COMPOST, AND METHOD FOR GROWING PLANT

(71) Applicant: SUNLIT SEEDLINGS LTD., Kyoto (JP)

(72) Inventor: Sota Ishikawa, Kyoto (JP)

(73) Assignee: SUNLIT SEEDLINGS LTD., Kyoto (JP)

( * ) Notice: Subject to any disclaimer, the term of this patent is extended or adjusted under 35 U.S.C. 154(b) by 468 days.

(21) Appl. No.: 18/002,375

(22) PCT Filed: Oct. 25, 2021

(86) PCT No.: PCT/JP2021/039307
§ 371 (c)(1),
(2) Date: Dec. 19, 2022

(87) PCT Pub. No.: WO2022/102389
PCT Pub. Date: May 19, 2022

(65) Prior Publication Data

US 2023/0263113 A1 Aug. 24, 2023

(30) Foreign Application Priority Data

Nov. 12, 2020 (JP) ................................ 2020-189038
Mar. 10, 2021 (JP) ................................ 2021-038477
Sep. 9, 2021 (JP) ................................ 2021-146540

(51) Int. Cl.
*A01G 23/00* (2006.01)
*A01G 18/10* (2018.01)
(Continued)

(52) U.S. Cl.
CPC ............ *A01G 23/00* (2013.01); *A01G 18/10* (2018.02); *A01H 17/00* (2013.01); *A01N 63/30* (2020.01)

(58) Field of Classification Search
None
See application file for complete search history.

(56) References Cited

U.S. PATENT DOCUMENTS 5,026,417 A * 6/1991 Kucey .................... A01N 63/36 435/933
5,770,787 A * 6/1998 Montague ................ A01C 1/06 435/243
(Continued)

FOREIGN PATENT DOCUMENTS

JP H09-084577 A 3/1997
JP 2001-231365 A 8/2001
(Continued)

OTHER PUBLICATIONS

Correction Request for Opposition 2022-700911 (U.S. Pat. No. 7,038,451).
(Continued)

*Primary Examiner* — Marisa V Conlon
(74) *Attorney, Agent, or Firm* — Rankin, Hill & Clark LLP

(57) ABSTRACT

A method for growing a seedling, the method includes specifying a growth-contributing fungus contributable to growth of a target plant to be grown artificially, isolating the growth-contributing fungus, culturing the isolated growth-contributing fungus to obtain an inoculum, growing the inoculum with a growth substrate to obtain a microorganism bed, and rooting and growing the target plant in compost including the microorganism bed. In the specifying a growth-contributing fungus contributable to growth of a target plant to be grown artificially, the growth-contributing fungus is an indigenous nonmycorrhizal filamentous fungus to inhabit a planting site in which the target plant is to be
(Continued)

planted or a neighborhood of the planting site and to live in symbiosis with a plant without a mycorrhiza.

6 Claims, 3 Drawing Sheets

(51) Int. Cl.
*A01H 17/00* (2006.01)
*A01N 63/30* (2020.01)

(56) References Cited

U.S. PATENT DOCUMENTS

| | | | | |
|---|---|---|---|---|
| 6,548,745 | B2 | 4/2003 | Hiruma et al. | |
| 8,278,247 | B2 * | 10/2012 | Hnatowich | A01N 63/36 504/117 |
| 8,569,037 | B2 * | 10/2013 | Tateishi | A01N 63/30 504/117 |
| 9,277,751 | B2 | 3/2016 | Sword | |
| 9,365,464 | B2 * | 6/2016 | Greenshields | C05G 3/00 |
| 2001/0032343 | A1 | 10/2001 | Hiruma et al. | |
| 2015/0126365 | A1 | 5/2015 | Sword | |
| 2020/0085067 | A1 * | 3/2020 | Profizi | A01N 63/36 |

FOREIGN PATENT DOCUMENTS

| | | | |
|---|---|---|---|
| JP | 2013-42695 | A | 3/2013 |
| JP | 2014-50401 | A | 3/2014 |
| JP | 2016-171787 | A | 9/2016 |
| JP | 2019-170179 | A | 10/2016 |
| JP | 2017-99376 | A | 6/2017 |
| JP | 6516252 | B2 | 5/2019 |
| WO | 98/42823 | A1 | 10/1998 |
| WO | 2017-188051 | A1 | 11/2017 |
| WO | 2020104501 | A1 | 5/2020 |

OTHER PUBLICATIONS

Remarks of Patentee for Opposition 2022-700911 (U.S. Pat. No. 7,038,451).

Demandee's Exhibit No. 1 of Remarks of Patentee for Opposition 2022-700911, Product Information of "ECOHOPE DJ" pp. 1-2, Kumiai Chemical Industry Co., Ltd., Web Site"https://www.kumiai-chem.co.jp/products/document/ecohopedj_wg.html".

Demandee's Exhibit No. 2 of Remarks of Patentee for Opposition 2022-700911,Catalog of "Torikodesoilu(Japanese in Roman characters)" of Arysta LifeScience Corporation.

Demandee's Exhibit No. 3 of Remarks of Patentee for Opposition 2022-700911, Product information of "Tafubulokku (Japanese in Roman characters)" of Kyoyu Agri Co., Ltd.

Demandee's Exhibit No. 4 of Remarks of Patentee for Opposition 2022-700911, Catalog of "Tafubulokku(Japanese in Roman characters)" of Kyoyu Agri Co., Ltd.

Demandee's Exhibit No. 5 of Remarks of Patentee for Opposition 2022-700911, Catalog of "Minitan(Japanese in Roman characters) WG" of ISK Biosciences K.K.

Remarks of Opponent for Opposition 2022-700911 (U.S. Pat. No. 7,038,451).

Additional Reference No. 3 of Remarks of Opponent for Opposition 2022-700911, Hirokazu Toju, "Integrating Ecology and Phylogeny on the basis of various species network", Nature Ecology & Evolution [online], Feb. 2017, URL: https://www.natureasia.com/ja-jp/natecolevo1/interview/contents/2.

Additional Reference No. 4 of Remarks of Opponent for Opposition 2022-700911, Kazuhiko Narisawa, "Collection of Dark—septate endophytic fungi from forest soil at the southwest subtropics in Japan", Microbial Genetic Resources Exploration and Collection Survey Report, pp. 1-6, vol. 21 issued on Dec. 26, 2008, Independent administrative institution of National Institute of Agrobiological Sciences.

Announcement of decision on Opposition 2022-700911 (U.S. Pat. No. 7,038,451).

Notification of decision on Opposition 2022-700911 (U.S. Pat. No. 7,038,451).

Extened European search report EP21891636 dated Sep. 13, 2024.

Marie Chave, Benjamin Perrin, Arnaud Dufils, Multiplier des champignons mycorhiziens sur son exploitation (suite de la fiche 1), Jul. 2017, XP055607336, Retrieved from the Internet: URL: https://geco.ecophytopic.fr/documents/20182/21720/pdf_Multiplier_des_champignons_mycorhiziens_sur_son_exploitation_1.pdf.

Khalil Kariman, Susan J. Barker, Ricarda Jost, Patrick M. Finnegan, Mark Tibbett, A novel plant-fungus symbiosis benefits the host without forming mycorrhizal structures, New Phytologist, vol. 201, No. 4, Nov. 27, 2013, pp. 1413-1422, XP093195810, https://doi.org/10.1111/nph.12600.

Jyunji Takenaga, The Effects of Mycotrophy Microbe on Horticulture Plant Growth, Bioindustry, vol. 14 No. 11 1997 p. 11-22.

Research and development strategies for plant-microflora interactions, Science and Technology Future Strategy Workshop Report (Japan) Mar. 2017.

Kei Hiruma and Yusuke Saijyo, Plant growth promotion by rhizosphere filamentous fungi under phosphorus nutrient depleted conditions, Jpn. J. Phytopathol. 84: 78-84 (2018).

Kei Hiruma, Nina Gerlach, Soledad Sacristan, Ryohei Thomas Nakano, Stephane Hacquard, Barbara Kracher, Ulla Neumann, Diana Ramirez, Marcel Bucher, Richard J. O'Connell, and Paul Schulze-Lefert, Root Endophyte Colletotrichum tofieldiae Confers Plant Fitness Benefits that Are Phosphate Status Dependent Cell, Oct. 7, 2016, vol. 165, No. 2, pp. 464-474.

Iwanami Dictionary of Biology, 3rd edition, 2nd printing, Japan, Iwanami Shoten Co. Apr. 20, 1984, pp. 643 left column, lines 40-50.

Kazuhiko Narisawa, Symbiotic microorganisms that protect crops; How Endophyte works and how to use it?, p. 16-p. 26, Dec. 31, 2011 1st printing, Rural Culture Association, Japan.

Teruyoshi Hashiba, Kazuhiko Narisawa and Tadayuki Shimanuki, Chemistry and Biology vol. 36, No. 11. 1998, p. 741-744, Japan.

Kazuhiko Narisawa,Fumiaki Usuki and Teruyoshi Hashiba, Studies on control of Chinese cabbage root-knot disease by root endophyte Heroconium chaeospira,Mar. 2007,p. 45-52,No. 10, Bulletin of the Plant Biotechnology Institute, Ibaraki Agricultural Center, Idbaraki Japan.

Yusuke Takashima, Hiroyuki Ota and Kazuhiko Narisawa, Do the endofungal bacteria control the nature of fungal endophytes?, Soil and Microorganisms vol. 69, No. 1 pp. 16-24 (2015).

Kei Hiruma and Yusuke Saijyo, Plant growth promotion by beneficial fungi in phosphate-starved conditions, Jpn. J.Phytopathol. 84:78-84 (2018).

Kazunori Sakamoto and Taeko Hagiwara, Screening of the Root Endophytic Fungi Which Promote the Growth of Cabbage Seedling, Japanese Journal of Soil Science and Plant Nutrition, vol. 72, No. 3, p. 429-431 (2001).

Joy Michal Johnson, Anatoli Lugwig, Alexandra C.U.Furch, Axel Mithofer, Sandra Scholz, Michael Reichelt and Ralf Olemüller, The Benefitial Root-Colonizing Fungus *Mortierella hyalina* Promotes the Aerial Growth of *Arabidopsis* and Activates Calcium-Dependent Responses That Restrict Alternaria brassicae-Induced Disease Development in Roots,Molecular plant-microbe interactions, vol. 32, No. 3, p. 351-363, 2019 Published, https://apsjournals.apsneto org/doi/epdf/10.1094/MPMI-05-18-0115-R.

Zahoor Ahmed Wani,Amit Kumar,Phalisteen Sultan,Kushal Bindu,Syed Riyaz-Ui-Hassan and Nasheeman Ashraf, Mortierella alpina CS10E4, an oleaginous fungal endophyte of *Crocus sativus* L.enhances apocarotenoid biosynthesis and stress tolerance in the host plant, Scientific reports, vol. 7 No. 1, p. I-11, 2017 Published, https://www.nature.com/articles/s41598-017-08974-z.pdf.

F. Liu1, G. Bonthond, J.Z.Groenewald, L. Cai and P.W. Crous, Sporocadaceae, a family of coelomycetous fungi with appendagebearing conidia, Studies in Mycology, 92, p. 287, Available online Nov. 17, 2018. https://doi.org/10.1016/1. simyco.2018.11.001.

International Search Report of PCT/JP2021/039307.

Written Opinion of the International Search Authority of PCT/JP2021/039307.

(56) References Cited

OTHER PUBLICATIONS

Notice of Reasons for Refusal Japanese Patent Application No. 2020-189038.
Notice of Reasons for Refusal Japanese Patent Application No. 2021-148604.
Patent Opposition Statement to Japanese Patent No. 7038451.
Notification of reasons for rescission for Japanese Patent No. 7038451.

* cited by examiner

[FIG. 1]
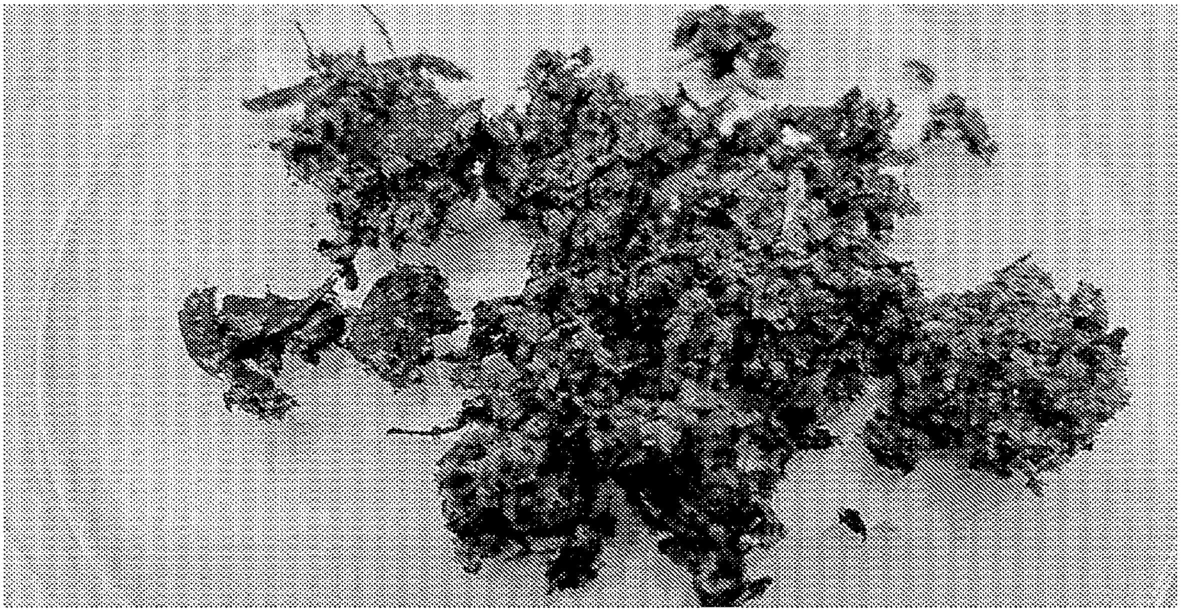
[FIG. 2]
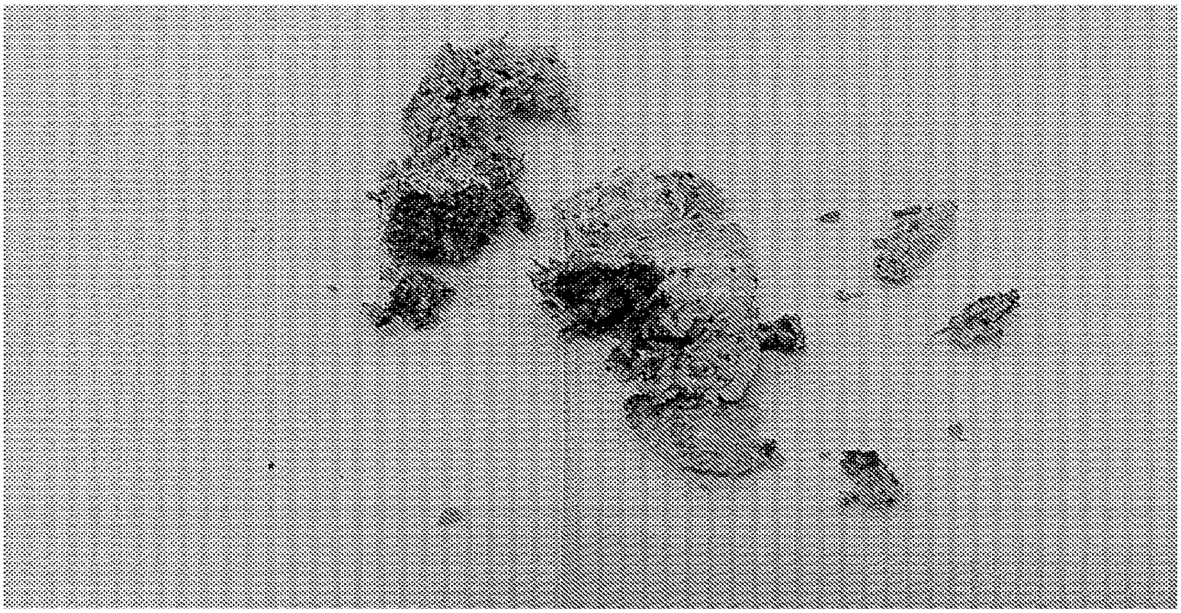

[FIG. 3]
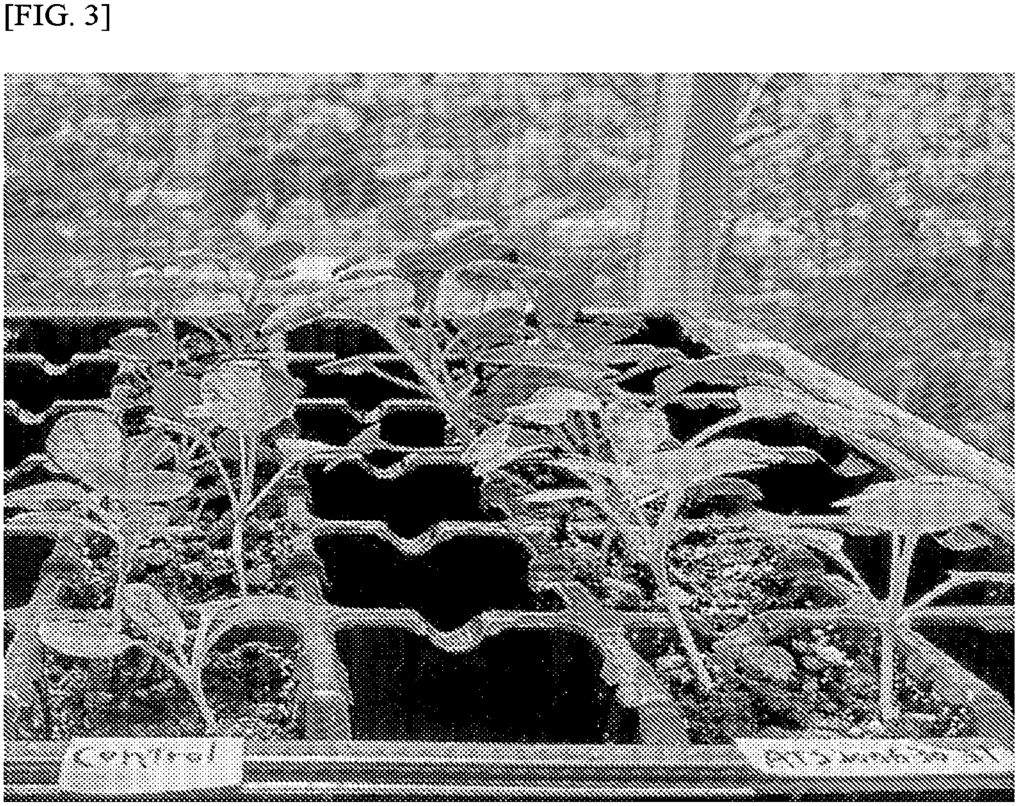
[FIG. 4]
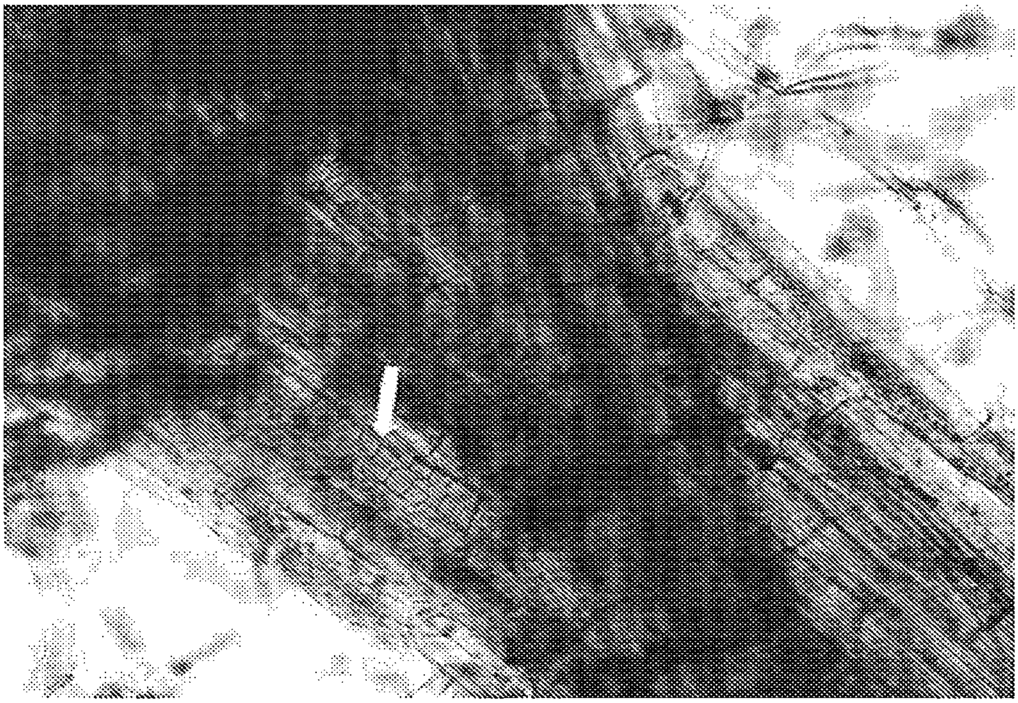

[FIG. 5]
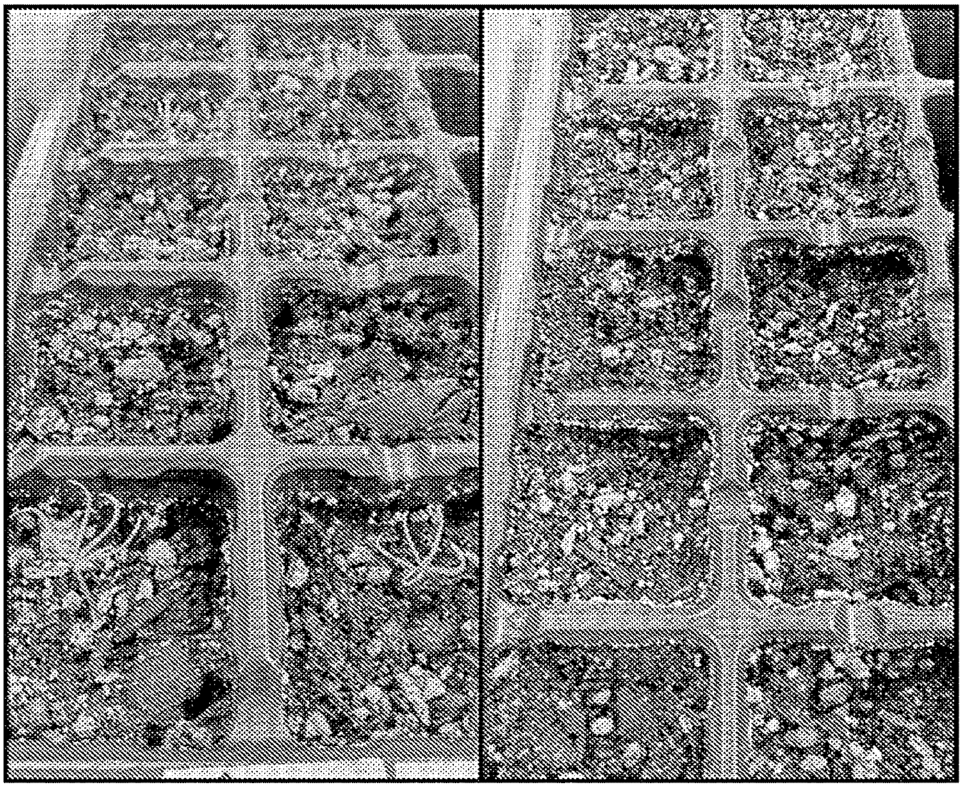
[FIG. 6]
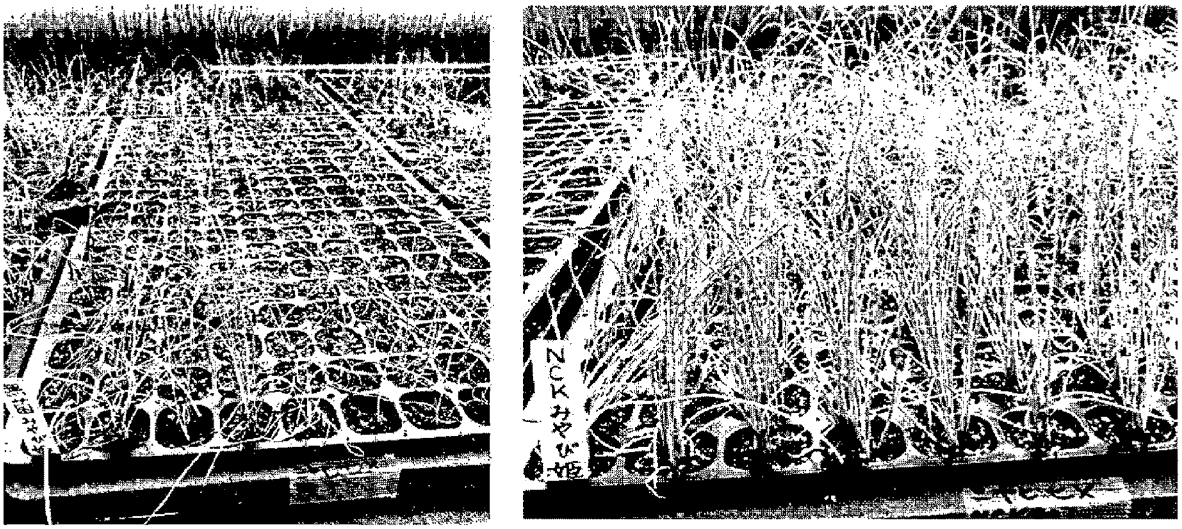

SEEDLING, METHOD FOR GROWING SEEDLING, COMPOST, AND METHOD FOR GROWING PLANT

FIELD

The present invention relates to a seedling for producing agricultural and forest products, a method for growing the seedling, compost, a method for growing a plant from a seedling, and in particular to a method for growing a plant using microorganisms.

BACKGROUND

In agriculture and forestry, typical plant cultivation includes planting seedlings that have grown to a specific size into agricultural or forest land and growing the plants until they can be harvested. Compared with directly sowing seeds on the agricultural or forest land, planting seedlings grown to a specific size in agricultural or forest land improves the germination rate and reduces a loss of early seedlings caused by, for example, insect pests.

Seedlings grown for planting include a seedling grown on the bare ground and a containerized seedling grown in a container (a tree seedling is also called a container seedling, and such a seedling is herein referred to as a containerized seedling). Containerized seedlings can be grown indoors, such as in a plastic greenhouse, throughout the year, or can be intensively grown in a narrow space. Thus, seedlings of many herbaceous plants such as vegetables or flowering plants are containerized. Containers for containerized seedlings typically having a capacity of about 50 to 350 ml are not suitable for growing plants that take a long time to grow. Thus, seedlings of woody plants that take about two years to grow have typically been bare-root seedlings grown on the bare ground. However, containerized seedlings of woody plants are also available for afforestation or gardening in recent years.

Well-grown seedlings are highly resistant to insect pests and other stresses after being planted, and thus growing such seedlings is intended. Increasing the germination rate of seeds sown can increase the number of seedlings yielded. Thus, methods have been developed for various species of plants for enhancing growth of seedlings or increasing the germination rate.

Plants (hereafter, target plants) are grown in, for example, farmland, gardens, or parks, using fertilizers that artificially promote plant growth, soil improvers that improve the physicochemical properties of soil, and pesticides that protect the plants from insect pests (hereafter, fertilizers, soil improvers, and pesticides may be collectively referred to as plant cultivation materials).

Of the plant cultivation materials, chemically synthesized fertilizers (chemical fertilizers) provide nutrients such as nitrogen or phosphorus to the plants in a form easily absorbable by the plants (specifically, as inorganic matter). Chemical fertilizers can thus easily function and have been widely used. Chemically synthesized pesticides (chemical pesticides) are chemical substances having the mechanism to destroy insects or microorganisms. The chemical pesticides function rapidly and reliably, similarly to the chemical fertilizers, and have been used widely.

These chemical fertilizers and chemical pesticides are used not to enhance the growth potential or stress resistance of the plants. Thus, some plant growing methods have been developed to grow healthy plants with high stress resistance by creating an environment that promotes healthy growth of plants without relying on chemical fertilizers or chemical pesticides.

Many methods for growing healthy plants focus on soil formulation. Soil serving as a bed for growing plants serves as a habitat for various organisms. The organisms inhabiting soil decompose the animal and plant residues contained in the soil (organic matter such as excrements of animals and fallen leaves, hereafter referred to as soil organic matter) into lower molecules. The nutrients such as nitrogen or phosphorus decomposed from the soil organic matter into the lower molecules are absorbable by the plants through the plant roots.

Healthy soil typically allows plants to root deeply with less stress, facilitates absorption of nutrients for growth, enhances growth of plants, and contains organisms that protect plants from pathogens. The soil is evaluated based on the physical structure, chemical characteristics, and biological characteristics. These elements interact with one another and thus are difficult to control artificially. In particular, the biological characteristics affected by microorganisms are not observable with the naked eyes and are difficult to control artificially.

In response to this, a known technique uses microorganisms for protection against pathogens as pesticides (Patent Literature 3). The microorganisms for protection against pathogens formulated into pesticides (microbial pesticides) have less impacts on ecosystems than chemical pesticides that can affect organisms other than pathogens. More specifically, microbial pesticides can avoid destroying organisms beneficial to plant growth while reducing pathogens. The microbial pesticides are thus suitable for formulating healthy soil that avoids the use of chemical pesticides or chemical fertilizers.

CITATION LIST

Patent Literature

Patent Literature 1: Japanese Patent No. 6516252
Patent Literature 2: Japanese Unexamined Patent Application Publication No. 2019-170179
Patent Literature 3: WO 2017/188051

SUMMARY

A method for growing a seedling in accordance with some embodiments comprises specifying a growth-contributing fungus contributable to growth of a target plant to be grown artificially, isolating the growth-contributing fungus, culturing the isolated growth-contributing fungus to obtain an inoculum, growing the inoculum with a growth substrate to obtain a microorganism bed, and rooting and growing the target plant in compost including the microorganism bed. In the specifying a growth-contributing fungus contributable to growth of a target plant to be grown artificially, the growth-contributing fungus is an indigenous nonmycorrhizal filamentous fungus to inhabit a planting site in which the target plant is to be planted or a neighborhood of the planting site and to live in symbiosis with a plant without a mycorrhiza.

BRIEF DESCRIPTION OF DRAWINGS

FIG. 1 is a photograph of a culture substrate of symbiotic microorganisms for preparing a microorganism bed used in Example 1.

FIG. 2 is a photograph of the microorganism bed used in Example 1.

FIG. 3 is a photograph of seedlings obtained in Example 1 (right column) and seedlings obtained in Comparative Example 1 (left column).

FIG. 4 is a photograph of filamentous fungi (a portion indicated by an arrow) of a symbiotic microorganism adhering to the root of a seedling obtained in Example 1.

FIG. 5 is a photograph of seedlings in Example 2 (two left columns) and Comparative Example 2 (two right columns), showing their growth states.

FIG. 6 is a photograph of containerized seedlings (Welsh onion) in Example 3 (on the right) and Comparative Example 3 (on the left), showing their growth states.

DESCRIPTION OF EMBODIMENTS

Patent Literature 1 describes a method for improving the growth of seedlings and the germination rate of specific plant species. Although the method for growing seedlings for specific plant species based on the characteristics of the plant species can appropriately improve the seedling growth, the method is to be designed for each of the different plant species. Patent Literature 2 describes a technique for growing tree seedlings that take a longer growing period. The technique may not be usable with vegetables, flowering plants, crops, or other herbaceous plants. Tree seedlings may be containerized for growth indoors. Of the seedlings of conifers for afforestation including Japanese cedar, Japanese cypress, Japanese pine, dark-bark spruce, Sakhalin fir, and Japanese larch, tree seedlings grown in a cold district such as Sakhalin spruce, dark-bark spruce, Dahurian larch, Sakhalin fir, and Japanese larch may be containerized for growth indoors throughout the year. However, tree seedlings that take a long growing period grown as containerized seedlings are more likely to grow poorly due to the shortage of compost.

As described in Patent Literature 3, similarly to chemical pesticides, microbial pesticides are typically distributed or applied as a liquid or mixed in materials such as a soil improver, or for example, compost or manure. The soil or plant bodies with the microbial pesticides contain various naturally occurring organisms, which may expel the distributed, applied, or mixed microorganisms. Thus, such microbial pesticides may not function sufficiently. To avoid microbial pesticides being expelled by naturally occurring organisms, the amount of pesticide to be distributed or applied may be increased.

In contrast to these known techniques, the seedling growing method according to one or more aspects of the present invention can promote the growth of seedlings of various plant species and yield good-quality seedlings without being limited to specific plant species, independently of whether the plant is herbaceous or woody. The method can also improve the germination rate of seeds sown and increase the yield rate. In particular, the seedling growing method according to one or more aspects of the present invention is applicable to, in addition to herbaceous plants that take several months to grow, woody plants that take one year or more to grow as well as to containerized seedlings produced indoors with a small amount of compost.

The seedling growing method according to one or more aspects of the present invention uses microorganisms. The method produces intended effects with a smaller amount of microorganisms used to, for example, promote the growth of a target plant.

One or more aspects of the present invention are directed to a seedling having a priority effect produced by specifying a symbiotic microorganism that can live in symbiosis with a target plant and promote the growth of the plant and by rooting the target plant in compost containing a mixture of a microorganism bed obtained by growing the symbiotic microorganism and a substrate for growing the plant to establish a symbiotic relationship between the target plant and the symbiotic microorganism. Other aspects of the present invention are directed to a method for growing such a seedling, compost for growing the seedling, and a method for growing a plant from the seedling.

The symbiotic microorganisms may be filamentous fungi that have the mycelia adhering to a plant root. Most microorganisms that have been industrially used for wastewater treatment or as a soil improver are unicellular microorganisms, including bacteria, yeasts, or actinomycetes that belong to bacteria. In contrast, industrial use of fungi among microorganisms has not advanced, although some species are used in mushroom cultivation. Most fungi are multicellular microorganisms with some species being exceptionally unicellular microorganisms such as yeasts. Multicellular fungi typically form a mycelium including a filament network of multiple cells. Unlike bacteria, yeasts, or actinomycetes, filamentous fungi included in multicellular microorganisms forming mycelia have the functions and ecology remaining unidentified and are not easy to handle. A method has thus been developed recently to analyze a microbiome that lives in symbiosis with plants and estimate microorganisms that can promote the growth of plants (Toju, H. et al., Core Microbiomes for Sustainable Agroecosystems. Nature Plants 2018, 4, 247-257, hereafter referred to as microbiome analysis by Toju), laying a base for identifying the functions or other characteristics of filamentous fungi in a microbiome.

In the study based on the microbiome analysis by Toju, the inventor of the present invention has found that filamentous fungi (specifically, isolate cultured-nonmycorrhizal filamentous fungi, described later) that can grow with easily accessible plant residues as a culture substrate include a filamentous fungus that lives in symbiosis with various plants and promotes the growth of the plants. The inventor has also found that the germination rate of seedlings can be improved and the growth of the seedlings can be promoted by rooting the target plant in a substrate of organic matter in which the filamentous fungi grown using the plant residues as the substrate extend, and thus completed the invention.

A method according to one or more aspects of the present invention includes specifying symbiotic microorganisms that can promote the growth of a target plant based on the microbiome analysis by Toju and with other methods, culturing the specified symbiotic microorganisms on a microorganism-culture substrate for growing the specified symbiotic microorganisms to extend mycelia, and mixing the symbiotic microorganisms with the extendable mycelia into compost for growing plants to root the target plant.

In one or more aspects of the present invention, the symbiotic microorganisms to be used may be specified from filamentous fungi included in soil microorganisms inhabiting a planting site in which the target plant is to be planted or its neighborhood.

The technique according to the above aspects of the present invention includes specifying symbiotic microorganisms that can promote the growth of a target plant, growing an inoculum obtained by isolating and culturing the specified symbiotic microorganisms on a culture substrate to extend the mycelia of the symbiotic microorganisms, and rooting the target plant while further extending the mycelia contained in the microorganism bed in compost. This allows the symbiotic microorganisms to live in symbiosis with the target plant in the rhizosphere of the target plant. The target plant that has established a symbiotic relationship with the symbiotic microorganisms in the rhizosphere after being rooted is promoted to grow. Planting seedlings into the compost in which the mycelia of the symbiotic microorganisms extend improve the germination rate. The seedlings obtained with the technique according to the above aspects of the present invention produce a priority effect by living in symbiosis with the symbiotic microorganisms after being rooted, thus establishing a symbiotic network with indigenous microorganisms in the planting site after being planted based on the symbiotic relationship with the symbiotic microorganisms. Microorganisms (core microorganisms) that can introduce an intended symbiotic network with indigenous microorganisms in a planting site in which the target plant is to be planted may be used as symbiotic microorganisms to improve the rooting or the growth of the planted target plant.

With the technique according to the above aspects of the present invention, the symbiotic microorganisms that are beneficial to a target plant are collected from a planting site in which the target plant is to be planted or from its neighborhood. The collected symbiotic microorganisms are isolated, cultured, and placed in an area in which plant roots extend with the mycelia of the symbiotic microorganisms extending. This allows the fungus bodies of the symbiotic microorganisms to invade into the roots of the target plants or establish a close relationship with the roots in the rhizosphere to artificially establish a symbiotic relationship between the target plant and the symbiotic microorganisms, thus producing the effects more reliably with a smaller amount of symbiotic microorganisms.

An embodiment of the present invention will now be described. In the embodiment of the present invention, symbiotic microorganisms that are beneficial to the growth of a target plant are specified before the plant is grown. Symbiotic microorganisms may be specified by, for example, field work to selectively collect symbiotic microorganisms living in symbiosis with plants expected to grow well with the symbiotic microorganisms, literature search to specify microorganisms that are reportedly beneficial to the target plant, using a microorganism database to specify microorganisms determined to be beneficial to the target plant, or using the analysis by Toju. Specifying the microorganisms refers to determining microorganism species to be beneficial to the target plant as symbiotic microorganisms with any of the above methods, including determining microorganism species expected to have positive effects on the target plant as symbiotic microorganisms, in addition to determining microorganisms identified as being beneficial to the target plant as symbiotic microorganisms.

After symbiotic microorganisms are specified, an isolate culture of the specified symbiotic microorganism is inoculated into a microorganism culture substrate as an inoculum and is cultured. The symbiotic microorganism used as the inoculum may be isolated and cultured after being collected from the soil in the agricultural or forest land (planting site) in which the target plant is to be cultivated or in the neighborhood of the planting site or collected from plants that grow in the soil. The neighborhood of the planting site may be a site in a natural environment similar to the environment of the planting site and has an established natural ecosystem that includes plants, or more specifically, an area having the weather conditions or natural vegetation similar to those in the planting site. The neighborhood may be a site within a radius of about 50 km from the planting site and expected to have vegetation naturally occurring in the planting site. Inoculums may be collected from the neighborhood (within a radius of 100 to 300 km from the planting site for Japan, or within a radius of about 500 km for an area being vast and contiguous at overseas) to avoid artificial disruption of genetic resources. The symbiotic microorganisms may be indigenous microorganisms inhabiting the planting sites or their neighborhood, or more specifically, indigenous filamentous fungi that form filamentous fungi.

More specifically, symbiotic microorganisms may include filamentous fungi (hereafter referred to as nonmycorrhizal filamentous fungi) expected to have their mycelia invadable into the plant root of a target plant or have a close symbiotic relationship with the target plant in the rhizosphere. The filamentous fungi may be artificially cultured alone using a typical medium (e.g., a potato dextrose agar, or PDA, medium or an oatmeal medium) or animal or plant residues as a substrate without a symbiont (mycorrhiza) living with a plant root. Some species of filamentous fungi establish a symbiotic relationship with a plant by forming a symbiont with the plant root referred to as a mycorrhiza (such fungi are referred to as mycorrhizal fungi). The mycorrhiza is a symbiont with a characteristic structure of the plant root and the mycelia integrated together, and classified into arbuscular mycorrhizal fungi referred to as endophytic fungi and ectomycorrhizal fungi that form mushrooms such as matsutake.

Such mycorrhizal fungi typically use plants to grow the filamentous fungi, and the plants use the filamentous fungi to grow (hereafter referred to as obligate symbiosis). Thus, such mycorrhizal fungi can be artificially grown only in symbiosis with the plant root, on a special medium, or with a special culture method. In contrast, nonmycorrhizal filamentous fungi can have their mycelia invading into the plant body without a mycorrhiza or have a close symbiotic relationship with the plant in the rhizosphere of the plant. Thus, the nonmycorrhizal filamentous fungi alone can be artificially and purely cultured (isolated) using a typical medium or animal or plant residues as a substrate without living in symbiosis with the plant root (hereafter referred to as isolate cultured fungi). Isolate cultured-nonmycorrhizal filamentous fungi decompose various animal or plant residues serving as soil organic matter as nutrients (decomposition substrates) into lower molecules and absorb the decomposition substrates to grow, and thus can use various animal or plant residues as growth substrates to grow rapidly. Nonmycorrhizal filamentous fungi can grow in large quantities in a short period on substrates with easy access or easy handing or under culture conditions with easy access or easy handling, as compared with mycorrhizal fungi.

Obligate-symbiosis mycorrhizal fungi are known to establish an interdependent symbiotic relationship with a plant and be typically beneficial to plant growth. In contrast, many isolate cultured-nonmycorrhizal filamentous fungi are undetermined as to whether they are beneficial for plant growth. Some may be pathogenic and cause disease that inhibits plant growth.

However, some isolate cultured-nonmycorrhizal filamentous fungi are beneficial to plant growth (promote growth, protect the plants against disease, or improve resistance to humidity stress or temperature stress). In particular, the present invention is complete with the finding that isolate cultured-nonmycorrhizal filamentous fungi of a genus that may damage plants include filamentous fungi contributing to plant growth depending on their system.

In other words, some species of isolate cultured-nonmycorrhizal filamentous fungi are beneficial to plant growth with their mycelia adhering to the plant root (hereafter referred to as growth-contributing fungi). Some other species of isolate cultured-nonmycorrhizal filamentous fungi (hereafter referred to as recruiter fungi) adhering to a plant root establish a network of the mycelia that promote plant growth in cooperation with other filamentous fungi (hereafter referred to as accompanying filamentous fungi) that contribute to plant growth, although the functions of the recruiter fungi are largely unidentified.

In the embodiment of the present invention, growth-contributing, isolate cultured-nonmycorrhizal filamentous fungi or recruiter, isolate cultured-nonmycorrhizal filamentous fungi may be particularly specified for each target plant as symbiotic microorganisms. The specified isolate cultured-nonmycorrhizal filamentous fungi may be caused to adhere to the plant root.

The growth-contributing and recruiter fungi may be endophytic and directly invade into the root of the target plant to live in symbiosis with the plant. Endophytic filamentous fungi are also referred to as endophytic fungi. The endophytic fungi can inhabit the rhizosphere of a plant (typically soil) to adhere to the plant root and invade into the plant body. In contrast, some nonmycorrhizal filamentous fungi symbiosis with a plant live in symbiosis with a plant root by closely interacting with the plant root in the rhizosphere of the plant without invading into the plant body (ectomycorrhizal). For either being endophytic or ectomycorrhizal, nonmycorrhizal filamentous fungi symbiosis with a plant may have a symbiotic mechanism to live with a plant different from the symbiotic mechanism of mycorrhizal fungi that form mycorrhizae. These nonmycorrhizal filamentous fungi that inhabit soil without mycorrhizae to decompose animal or plant residues as nutrients may be also referred to as soil fungi or saprophytes. However, filamentous fungi vary in the form or the method of nutrition intake depending on the conditions. Thus, growth-contributing, isolate cultured-nonmycorrhizal filamentous fungi and recruiter, isolate cultured-nonmycorrhizal filamentous fungi are difficult to specify based on known classifications including, for example, soil fungi, saprophytes, or endophytic fungi or the latest classification system. Depending on the plant species or environmental conditions, isolate cultured-nonmycorrhizal filamentous fungi and a plant may have a symbiotic relationship that is mutually beneficial or a relationship in which filamentous fungi cause disease of the plant (or filamentous fungi may serve as disease fungi).

For filamentous fungi other than, for example, mycorrhizal fungi having the system or the relationship with plants being clearly identified, attempts to promote the growth of plants using filamentous fungi often may not yield expected results. Thus, filamentous fungi have not been used for plant growth. In contrast, the technique according to one or more embodiments of the present invention specifies, for each target plant, filamentous fungi beneficial to the growth of the target plant using, for example, the microbiome analysis by Toju, a filamentous fungus database, or inoculation tests of filamentous fungi on the plants, and allows the plant root to extend while growing the specified growth-contributing filamentous fungi in the rhizosphere of the plant. This allows the plant growth to be promoted more effectively and stably using filamentous fungi that vary more widely and are easier to handle than mycorrhizal fungi.

Microorganisms that are less likely to live directly with a target plant but contribute to the growth of the target plant are distinguished as accompanying fungi. More specifically, growth-contributing filamentous fungi and recruiter filamentous fungi may be nonmycorrhizal filamentous fungi, whereas accompanying filamentous fungi may not be nonmycorrhizal filamentous fungi. In one or more embodiments of the present invention, multiple species of symbiotic microorganisms may be specified. For example, recruiter, isolate cultured-nonmycorrhizal filamentous fungi and accompanying filamentous fungi may be specified as symbiotic microorganisms to prepare a microorganism bed using the inoculum obtained by isolating each fungus.

In particular, growth-contributing fungi may be specified from indigenous nonmycorrhizal filamentous fungi inhabiting a planting site or its neighborhood by, for example, analyzing a soil microbiome in the planting site in which the target plant is grown until being harvested. The specified fungi may be isolated to live in symbiosis with the target plant. The neighborhood refers to an area within a radius of 100 to 300 km from the planting site (or within a radius of about 500 km for the same ecosystem extending over vast and contiguous land). The analysis of the soil microbiome in the planting site or in its neighborhood can narrow the range of growth-contributing nonmycorrhizal filamentous fungi to be specified from thousands or tens of thousands of nonmycorrhizal filamentous fungi.

Indigenous microorganisms inhabiting the planting site or its neighborhood are adapted to the environment of the planting site and can easily produce their effects. Using such indigenous microorganisms may also prevent artificial disruption of genetic resources. When samples are collected from the planting site or from its neighborhood to use a filamentous fungus isolated from this sample as an inoculum, growth-contributing filamentous fungi can be specified without analyzing the soil microbiome in the planting site or in its neighborhood. However, analyzing the soil microbiome in the planting site or in its neighborhood allows species of disease fungi in the planting site or in its neighborhood to be estimated easily, and allows species of growth-contributing fungi for protection against the disease fungi to be estimated easily, thus allowing the growth-contributing filamentous fungi to be specified easily. Soil in the planting site also includes an artificial soil alternative to be used for the planting site that is a cultivation facility.

The preparation of an inoculum and the preparation of compost will now be described. Isolate cultured-nonmycorrhizal filamentous fungi can be isolated using a typical microorganism-culture medium and grown alone artificially, or in other words, can be purely cultured into an inoculum. More specifically, a sample containing isolate cultured-nonmycorrhizal filamentous fungi specified as symbiotic microorganisms is cultured on a typical medium for filamentous fungi (e.g., a PDA medium), and the obtained fungal body is transplanted to a medium for isolation (a typical filamentous-fungi medium such as a PDA medium) to be purely cultured into an inoculum. A sample collected from the planting site or from its neighborhood may be used to isolate indigenous isolate cultured-nonmycorrhizal filamentous fungi. The isolated strain undergoes DNA analysis, morphology observation, or an inoculation test to determine whether the isolated strain is a symbiotic microorganism (particularly, a growth-contributing nonmycorrhizal filamentous fungus) usable with the technique in one or more embodiments of the present invention. The inoculum of the microorganism can be obtained in this manner.

In one or more embodiments of the present invention, growth-contributing, isolate cultured-nonmycorrhizal filamentous fungi or recruiter, isolate cultured-nonmycorrhizal filamentous fungi contained in the sample collected from the planting site in which a target plant is grown or from its neighborhood are isolated using a typical microorganism medium to prepare a microorganism bed using the cultured inoculum.

Isolate cultured-nonmycorrhizal filamentous fungi can be grown using, as a substrate, organic residues serving as soil organic matter such as humus, sawdust, or manure and containing nutrients used for the growth of microorganisms such as nitrogen or phosphorus. Such organic residues are less expensive than a culture substrate (medium) and allow easy access and handling. Thus, the inoculum isolated from a sample and cultured may be inoculated into the organic residues serving as a growth substrate to grow and increase the mycelia to prepare the microorganism bed.

The microorganism bed may include symbiotic microorganisms cultured and extending their mycelia on a substrate mainly containing breathable plant residues with addition of nutrients (nitrogen and phosphorus). The substrate for microorganism growth for growing symbiotic microorganisms may contain more nitrogen and phosphorus than compost for growing the plant. The substrate for microorganism growth may be either liquid or solid, and may be, for example, a commercially available microorganism culture substrate used for inoculum preparation or a liquid fertilizer for plants. In some embodiments, the growth substrate may be prepared from organic residues mainly containing plant residues that are easily accessible and usable as a soil improver. More specifically, breathable plant residues may be a mixture of a main plant residue, serving as a carbon source such as humus, wood chips, husks of plants including chaff or coconut shells, or rice straw, with a nourishing plant residue containing rice bran or bran as nutrients. In some embodiments, a fertilizer or a solution serving as a source of nutrients such as nitrogen or phosphorus may be mixed with a carbon source. The substrate for microorganism growth may be prepared to contain 0.5 to 1.5 mass % of nitrogen, or specifically about 0.6 to 1 mass % of nitrogen, 0.8 to 2 mass % of phosphorus, or specifically about 1 to 1.5 mass % of phosphorus, and 0.4 to 1.2 mass % of potassium, or specifically about 0.5 to 0.7 mass % of potassium.

When a solid plant residue mixture is used as an inoculum growth substrate, plant residues with breathable spaces, such as humus including a mixture of plant pieces, grains, and powder, may be inoculated with symbiotic microorganisms to allow the symbiotic microorganisms to extend their mycelia without anaerobic portions. When having no anaerobic portions, the breathable growth substrate contains appropriate moisture (about 10 to 40 mass %, or specifically about 15 to 30 mass %) without forming clumps through water absorption and can crumble when loosened with hands. The substrate may have a thickness not exceeding about 5 cm, or specifically, about 1 to 2 cm to allow mycelia to extend.

In particular, the growth substrate containing moisture and being wet enough to crumble when loosened with hands may be sterilized and inoculated with isolated and cultured inoculum (symbiotic microorganisms). The growth substrate such as humus contains various microorganisms. The growth substrate may be sterilized to eliminate or inactivate microorganisms other than inoculum before being inoculated with the inoculum. The sterilized growth substrate includes the inoculum dominant in the growth substrate and allows the mycelia of the inoculum to extend easily. Some inoculums may not use sterilization. The inoculum may have the volume ratio of about 0.1 to 5 to the growth substrate of 100. A substrate having a small quantity of inoculum inoculated takes a long culture time to yield the microorganism bed, whereas a substrate having a large quantity of inoculum inoculated excessively increases the quantity of inoculum used to prepare the microorganism bed.

The growth substrate inoculated with the inoculum is cultured at normal temperature (about 15 to 30° C.) to grow symbiotic microorganisms to prepare a microorganism bed on which the symbiotic microorganisms are dominant. To allow symbiotic microorganisms to be dominant, the growth substrate inoculated with the inoculum may be cultured under aerobic conditions for about a half day to 15 days, or specifically, about one day to seven days. In particular, to allow filamentous fungi serving as symbiotic microorganisms to be dominant, the growth substrate inoculated with the inoculum may have no clump forming through water absorption, allow the inoculum to be fully exposed to natural ventilation, and allow the mycelia of the symbiotic microorganisms to extend in the growth substrate.

The symbiotic microorganisms being dominant in the microorganism bed herein refers to the symbiotic microorganisms with the maximum relative ratio in the DNA analysis of the microbiome in the microorganism bed. The symbiotic microorganisms being dominant in the microorganism bed also refers to, as another index, the symbiotic microorganisms with the inoculated filamentous fungi extending and forming clumps on the growth substrate with no clump before being inoculated with symbiotic microorganisms, or refers to the symbiotic microorganisms with the fungus bodies visibly observed in the growth substrate.

The microorganism bed containing symbiotic microorganisms extending their mycelia is mixed with the plant-growth substrate to be compost. The target plant is then rooted in the compost with the mycelia of the symbiotic microorganisms extending in the compost. Although not limited to a particular substrate, the plant-growth substrate may include organic matter to allow the symbiotic microorganisms to extend their mycelia. In particular, when isolate cultured-nonmycorrhizal filamentous fungi are used as symbiotic microorganisms, the substrate may contain organic matter serving as decomposition substrates of the fungi. Although the plant-growth substrate may contain mineral matter such as pearlite or red clay, a substrate containing organic matter alone without containing mineral matter may be used to reduce weight. Although the plant-growth substrate may use, as its organic matter, the same plant residues as used for the microorganism bed, the organic matter may be plant residues convenient as plant compost, or for example, fruit residues such as coconut shells or coco peat or plant residues such as cut pieces of supporting tissue including rice straws, wheat or barley straws, stems of other plants, or bark. The plant-growth substrate may be more oligotrophic than the culture substrate for preparing the microorganism bed and is usable without adding nutrients to the plant residues serving as carbon sources. Compost prepared by mixing the plant-growth substrate with the microorganism bed may contain 0.1 to 0.8 mass % of nitrogen, or specifically about 0.3 to 0.6 mass % of nitrogen, 0.2 to 1 mass % of phosphorus, or specifically about 0.3 to 0.8 mass % of phosphorus, and 0.1 to 0.7 mass % of potassium, or specifically about 0.2 to 0.5 mass % of potassium.

The compost may contain the microorganism bed at a capacity ratio of about 5 to 50% inclusive, or specifically about 10 to 30% inclusive. To reduce the adjustment cost (time and labor), the compost may contain microorganisms other than the inoculum without being sterilized. For such unsterilized compost, a small amount of microorganism may not allow the inoculum to grow fully, and a large amount of inoculum may use a large amount of the microorganism bed. When isolate cultured-nonmycorrhizal filamentous fungi are used as symbiotic microorganisms, the compost is to contain a growth substrate for nonmycorrhizal filamentous fungi. Thus, the compost may contain organic matter serving as the growth substrate of fungi at a capacity ratio of about 3 to 30% inclusive, or more specifically about 5 to 15% inclusive, with nutrients including nitrogen, phosphorus, and potassium adjusted to be in the above quantities.

Any rooting source such as a seed, a cutting, a herbaceous cutting, or vegetable tissue is placed in the compost prepared in the manner described above. The temperature or moisture is adjusted for rooting conditions to allow the rooting source of a target plant to root in the compost. The rooting source may be of any plant body (including a vegetable cell) that causes a plant to root.

The plant-growth compost that does not involve sterilization is more easily prepared in a large amount than the microorganism bed. The microorganism bed may be prepared on the sterilized growth substrate at a small amount for growing seedlings. The microorganism bed may thus be mixed into the compost uniformly at about a capacity ratio of 5 to 30 to the entire compost or may be located to surround the rooting source (for example, within a radius of about 1 to 3 cm from the rooting source). In particular, when isolate cultured-nonmycorrhizal filamentous fungi are used as symbiotic microorganisms, the inoculum obtained through isolation and pure culture on a typical medium with a typical culture method can extend and grow their mycelia with the growth substrate such as humus. The microorganism bed obtained by growing the inoculum with the growth substrate functions as plant growth compost that allows easy access and handling. In this microorganism bed, the inoculum grows mycelia. When the microorganism bed is placed to allow the root of the target plant to extend while the mycelia derived from the inoculum are growing, the inoculum can grow the mycelia to have a symbiotic relationship more reliably with the target plant, although the amount of microbial inoculant (microorganism bed) is small.

In several days to several weeks after the growing plant starts rooting in the compost (specifically, the rooting source is placed into the compost to be ready to root), the mycelia derived from the symbiotic microorganisms serving as inoculums can extend in the rhizosphere of the target plant to establish a symbiotic relationship with the target plant. The period taken for the mycelia to adhere to the plant root from the start of rooting varies depending on, for example, the plant species, the rooting source, or the temperature condition. The mycelia adhering to the root refers to the mycelia of symbiotic microorganisms invading into cells or spaces between cell walls of the root of the target plant in compost (endophytic) or the mycelia adhering to the surface of the root (ectomycorrhizal).

In one or more embodiments of the present invention, isolate cultured-nonmycorrhizal filamentous fungi may be used as symbiotic microorganisms. When multiple species of symbiotic microorganisms are used, the symbiotic microorganisms include at least a growth-contributing, isolate cultured-nonmycorrhizal filamentous fungus or a recruiter, isolate cultured-nonmycorrhizal filamentous fungus and one or more accompanying filamentous fungi. Mycorrhizal fungi typically live with a limited host (symbiont), and are difficult to culture artificially without a host. Mycorrhizal fungi are to live in symbiosis with the plant root or involve a special culture method or a special medium. Thus, symbiosis between mycorrhizal fungi and a target plant includes an advanced technical operation.

In contrast, isolate cultured-nonmycorrhizal filamentous fungi can be purely cultured in a typical microorganism medium and can extend their mycelia in a substrate including sterilized or unsterilized organic matter used as typical plant cultivation materials such as humus. Some nonmycorrhizal filamentous fungi have low host specificity and can invade into roots of various species of target plants. Other nonmycorrhizal filamentous fungi have high host specificity, with high contribution to the growth of the host.

The isolate cultured-nonmycorrhizal filamentous fungi used in one or more embodiments of the present invention as symbiotic microorganisms to live in symbiosis with the root of the target plant may include isolate cultured-nonmycorrhizal filamentous fungi having either low or undetermined contribution to the growth of the target plant but having low host specificity (specifically, recruiter fungi). In some embodiments, growth-contributing, isolate cultured-nonmycorrhizal filamentous fungi with high host specificity may be used as symbiotic microorganisms. In either case, the operations performed after the symbiotic microorganisms are specified (preparation of an inoculum, preparation of a microorganism bed from the inoculum, and placement of the microorganism bed into rhizosphere) remain the same as described in the embodiments of the present invention. Thus, for any target plants, the same procedure or materials for growing seedlings or plants may be used to facilitate the process of growth of a plant, preparation of plant cultivation materials, or scale expansion or simplification of the method to be used.

Isolate cultured-nonmycorrhizal filamentous fungi may be either endophytic fungi that invade into the bodies of plants or ectomycorrhizal fungi that adhere to plants without invading into the bodies of the plants. Endophytic fungi, which can couple with the plant roots more firmly than ectomycorrhizal fungi, may be used.

To cause the mycelia derived from the symbiotic microorganism to adhere to the roots of the target plant, symbiotic microorganisms contained in the microorganism bed may extend their mycelia in the rhizosphere when the target plant roots or extends in compost. More specifically, compost may be prepared using the microorganism bed obtained within two weeks or a week after the growth substrate is inoculated with an inoculum and the symbiotic microorganisms start growing. A rooting source may be placed into the prepared compost without delay, or more specifically, on the day of preparing the compost, the next day, or two days later at latest. After the rooting source is placed in the compost, watering and other processes may be performed without delay, or more specifically, on the day of placing the rooting source in the compost or the next day at latest, to cause the rooting source to start rooting or to extend the root.

The target plant may be grown into a seedling in the compost containing symbiotic microorganisms, or particularly, growth-contributing, isolate cultured-nonmycorrhizal filamentous fungi. The seedling may then be planted in the planting site to grow. In particular, growing seedlings using a seedling growth container saves the amount of compost and reduces the likelihood of the early seedlings being contaminated by disease fungi in the seedling rhizosphere in the planting site. The seedlings living in symbiosis with the growth-contributing inoculums grow well in the early stage. Thus, robust and early-grown (specifically, ready to be planted early) seedlings can be obtained.

The seedling of the target plant may be grown in the compost in the breathable state. When the seedling is grown in the compost placed in the container, a breathable container may be used. Examples of the breathable container include a slit container having ventholes on the side surfaces and a breathable plant container formed by molding plant pieces into a container shape. In one or more embodiments of the present invention, a tree seedling can be healthily grown in a small container with a capacity of about 50 to 350 ml. The seedling growth container may have any size or any shape, and may be a planter with a capacity of several thousands of milliliters.

When the seedling in the container is grown to a size appropriate for planting, the seedling can be planted outdoors or in a facility field. The seedling obtained according to one or more embodiments of the present invention has an established symbiotic relationship with symbiotic microorganisms from when the seedling is rooted, with the presence of the mycelia of the symbiotic microorganisms that promote the growth in the rhizosphere. Symbiotic microorganisms as prior residents live in symbiosis with the seedling. After the seedling is planted, the symbiotic microorganisms affect the symbiotic relationship between the seedling and the indigenous microorganism inhabiting the rhizosphere (priority effect). Thus, symbiotic microorganisms can promote the growth of the seedling also after the seedling is planted. When microorganisms (core microorganisms) that are compatible with a microbiome in the planting site, or more specifically, microorganisms that contribute to the growth of the seedling, are used as symbiotic microorganisms, the core microorganisms promote establishment of an intended symbiotic network with the indigenous microorganism after the seedling is planted and promote intended growth of the seedling.

The plant growing method using microorganisms according to one or more embodiments of the present embodiment includes placing the above microorganism bed or compost (hereafter referred to as a symbiotic microorganism-containing material) within a range in which the root of the target plant extends. More specifically, for seedlings rooted from vegetable tissue such as a plant seed or branch, the seedling or the cutting is rooted particularly in a container containing the compost, thus using a small amount of compost. To artificially establish a symbiotic relationship between a seedling and symbiotic microorganisms during preparation of the seedling, the mycelia may extend in the compost mixed with the microorganism bed to allow the plant to root.

The target plant may be grown in the soil of outdoor agricultural or forest land without using a container. Various organisms inhabit the outdoor agricultural or forest land other than symbiotic microorganisms. Thus, although compost or a culture liquid containing symbiotic microorganisms is scattered on or mixed into the soil as with typical plant cultivation materials, symbiotic microorganisms may be defeated by the indigenous organisms in the soil without establishing a symbiotic relationship with the target plant.

In one or more embodiments of the present invention, the above symbiotic microorganism-containing material is placed in the rhizosphere in which the plant root extends. This allows the plant root and the mycelia of the symbiotic microorganisms to extend in the symbiotic microorganism-containing material to cause the mycelia to invade into the root of the target plant, thus artificially establishing the symbiotic relationship between the symbiotic microorganisms and the target plant.

Example 1

In Example 1, seedlings of komatsuna, a species of herbaceous plant, were grown as a target plant. The microorganisms used as the symbiotic microorganisms that promote the growth of komatsuna were microorganisms isolated as samples from a plant that has grown with an established symbiotic relationship with the microorganisms. The plant was found during field work on the bare ground containing mineral matter soil (a B layer) being exposed. The samples were collected from an area including the planting site (within a radius of about 30 km from the site) in which Dahurian larch grown in Example 2 is to be planted. Of the isolated microorganisms, filamentous fungi of the family Sporocadaceae classified into ascomycetes were specified as symbiotic microorganisms by referring to, for example, literature. Filamentous fungi isolated using a PDA medium were purely cultured on an oatmeal medium to be an inoculum, and inoculated into a substrate as a growth substrate used to grow the inoculum. The substrate was obtained by mixing rice bran and bran serving as nutrients into humus serving as a carbon source. Humus had a carbon-to-nitrogen (C/N) ratio of 30 and a nitrogen content of 0.4 mass %. The growth substrate prepared by mixing nutrients into the humus contained, per 100 g, 12 g of a carbon source, 0.884 g of nitrogen, 1.364 g of phosphoric acid, and 0.656 g of potassium. To 200 ml of the growth substrate, 50 ml of water was added and mixed to allow the growth substrate to be wet enough to crumble when loosened with hands (FIG. 1). The growth substrate was sterilized in an autoclave. Two hundreds milliliters of the sterilized growth substrate was inoculated with an oatmeal agar medium piece (about 5×5 mm) serving as an inoculum, in which the isolated filamentous fungi are cultured. The substrate inoculated with the inoculum was cultured at room temperature (about 25° C.) for three days to produce a microorganism bed.

The obtained microorganism bed formed clumps with the presence of mycelia of inoculated filamentous fungi, and was visually determined to have the fungus bodies of the filamentous fungi on the surface (FIG. 2). Two hundreds milliliters of the plant-growth substrate was mixed into 10 ml of the obtained microorganism bed to produce compost. The plant-growth substrate used was unfertilized gardening soil (with the product name of Ginnotsuchi) mainly containing mineral matter such as pumice or pearlite. The prepared compost was placed into joint pots for seedling growth (each pot has a capacity of 80 ml), and a komatsuna seed was sown in each pot without delay. After sown, komatsuna was watered and left at room temperature and started rooting.

Comparative Example 1

Experiments were conducted in Comparative Example 1 under the same conditions as in Example 1 except that the plant-growth substrate used in Example 1 was not mixed with the microorganism bed.

FIG. 3 shows komatsuna seedlings grown in Example 1 and Comparative Example 1 20 days after the start of rooting (specifically, after sowing). As shown in FIG. 3, the seedlings on the right grown in Example 1 were grown better than the seedlings on the left grown in Comparative Example 1. The roots of the seedlings grown in Example 1 and Comparative Example 1 were stained and observed with a microscope. The mycelia derived from the symbiotic microorganisms invaded into the spaces between the cells at the roots of the seedlings grown in Example 1 to cover the cell surfaces. The mycelia adhered to the roots of the komatsuna seedlings (FIG. 4). In contrast, no adhesion of mycelia of filamentous fungi was observed at the roots of the seedlings in Comparative Example 1, unlike at the roots of the seedlings in Example 1.

Example 2

In Example 2, seedlings of Dahurian larch serving as afforestation conifer seedlings were grown as a target plant. The same conditions were used as in Example 1 except that the target plant was Dahurian larch.

Comparative Example 2

In Comparative Example 2, the seedlings of Dahurian larch were grown in the compost used in Comparative Example 1. The same conditions were used as in Comparative Example 1 except that the target plant was Dahurian larch.

In Example 2, of the ten cell pots sown with Dahurian larch seeds, three seedlings germinated 20 days after the start of rooting (specifically, after sowing). In Comparative Example 2, of the ten cell pots sown with Dahurian larch seeds, no seedling germinated 20 days after the start of rooting. In Example 2, the Dahurian larch seedlings 30 days after the start of rooting were grown to 3 to 4 cm as shown in FIG. 5 on the left. In Comparative Example 2, seeds in some cell pots cracked and almost germinated, but not completely germinated 30 days after the start of rooting as shown in FIG. 5 on the right.

As described above, the technique according to one or more embodiments of the present invention can improve the germination rate in growth of seedlings and promote the growth of seedlings.

Example 3

In Example 3, the field in which the Welsh onion is grown year round (successively) was used as the planting site, and a soil microbiome was analyzed through environmental DNA analysis at the planting site. The soil microbiome analysis at the planting site shows that the soil contained pathogenic fungi for the Welsh onion such as *Fusarium* genus and *Alternaria* genus. Literature search and an inoculation test show that the soil contained fungi of *Mortierella* genus to be growth-contributing nonmycorrhizal filamentous fungi that promote the growth of the Welsh onion. Thus, the site about 200 km away in a linear distance from the planting site but contiguous with the site was determined as the neighborhood of the planting site, and multiple isolate cultured-nonmycorrhizal filamentous fungi were isolated from samples collected from the forest soil in the neighborhood. The strain identified as belonging to *Mortierella* genus through the morphology observation and the DNA analysis on the isolated strain was used as growth-contributing nonmycorrhizal filamentous fungi.

Rice bran was added to compost of a waste culture medium (with the product name of MASH ORG) serving as a substrate for growing an inoculum. The inoculum was inoculated into the substrate in the same manner as in Example 1 to prepare a microorganism bed. In Example 3, a growth substrate was inoculated with the inoculum without being sterilized. The plant-growth substrate used was the same waste culture medium compost as for the substrate for growing the inoculum. The compost was not mixed with rice bran and not sterilized. To prepare seedling growth compost, 4 L of the plant-growth substrate was mixed with 1 L of the microorganism bed at a capacity ratio. The obtained seedling growth compost was placed into a seedling growth plate with 200 holes and was sown with seeds to grow seedlings.

Comparative Example 3

The same seedling growth compost as in Example 3 except that the compost contains no microorganism bed was used, and sowing and growing the seedlings of the Welsh onion were performed under the same conditions as in Example 3.

FIG. 6 shows seedlings grown in Example 3 and Comparative Example 3. The seedlings in the left tray in FIG. 6 are seedlings in Comparative Example 3, and the seedlings in the right tray in FIG. 6 are seedlings in Example 3. The experiments in Example 3 and Comparative Example 3 were conducted at high temperature and humidity (summer) that is harsh for the growth of the Welsh onion seedlings. Thus, about 150 seedlings of 200 seedlings in Comparative Example 3 died. In contrast, about 50 seedlings died in Example 3. The seedlings in Example 3 grew better than the seedlings in Comparative Example 3.

What is claimed is:

1. A method for growing a seedling, the method comprising:

collecting soil from a planting site in which a target plant to be grown artificially is to be planted or a neighborhood of the planting site;

performing an environmental DNA analysis of a soil microbiome contained in the collected soil, and specifying, based on a result of the environmental DNA analysis, a growth-contributing fungus contributable to growth of the target plant, the growth-contributing fungus being an indigenous nonmycorrhizal filamentous fungus that inhabits the planting site or the neighborhood of the planting site and lives in symbiosis with a plant without a mycorrhiza;

isolating the growth-contributing fungus from the collected soil;

culturing the isolated growth-contributing fungus to obtain an inoculum;

growing the inoculum with a growth substrate to obtain a microorganism bed; and rooting and growing the target plant in compost including the microorganism bed.

2. The method according to claim 1, wherein the method further comprises rooting and growing the target plant in a container containing the compost, thereby obtaining a containerized tree seedling.

3. The method according to claim 1, wherein the seedling is a coniferous seedling for afforestation.

4. A seedling obtained with the method according to claim 1.

5. A method for growing a plant, the method comprising:

planting and growing the seedling according to claim 4 in the planting site.

6. A seedling obtained with the method according to claim 3.

* * * * *